United States Patent [19]

Webb et al.

[11] 4,430,061
[45] * Feb. 7, 1984

[54] ORTHODONTIC BRACKET ASSEMBLY

[75] Inventors: David E. Webb, Jamul; Lawrence F. Andrews, San Diego, both of Calif.

[73] Assignee: Johnson and Johnson, New Brunswick, N.J.

[*] Notice: The portion of the term of this patent subsequent to Jan. 18, 2000 has been disclaimed.

[21] Appl. No.: 420,677

[22] Filed: Sep. 21, 1982

Related U.S. Application Data

[63] Continuation-in-part of Ser. No. 203,826, Nov. 3, 1980, Pat. No. 4,369,033.

[51] Int. Cl.³ .............................................. A61C 3/00
[52] U.S. Cl. ...................................................... 433/9
[58] Field of Search ........................ 433/9; 51/313, 422

[56] References Cited

U.S. PATENT DOCUMENTS

| | | | |
|---|---|---|---|
| 3,543,452 | 12/1970 | Guenther | 51/313 |
| 3,765,091 | 10/1973 | Northcutt | 433/9 |
| 3,975,824 | 8/1976 | Lee | 433/14 |
| 4,100,678 | 7/1978 | Yatabe | 433/9 |
| 4,165,561 | 8/1979 | Miller et al. | 433/9 |
| 4,243,386 | 1/1981 | Kawaguchi | 433/9 |
| 4,369,033 | 1/1983 | Webb et al. | 433/9 |

Primary Examiner—John J. Wilson
Attorney, Agent, or Firm—Townsend & Townsend

[57] ABSTRACT

An orthodontic bracket assembly for bonding to the surface of a tooth is disclosed. The assembly includes a pad and an archwire bracket. A plurality of cavities are provided in the tooth abutting surface of the pad. The walls of the cavities are provided with an irregular surface texture to enhance the bonding between the tooth and the orthodontic bracket. In the preferred embodiment the bracket is cast. The external surface of the bracket is smoothed in a tumbling operation in which the particle size of the abrasive is chosen so that the cavity walls are not subjected to treatment but are left in their irregular, as-cast state. Also disclosed is a method for preparing the mold to produce the cavities in the tooth-abutting surface of the pad.

6 Claims, 5 Drawing Figures

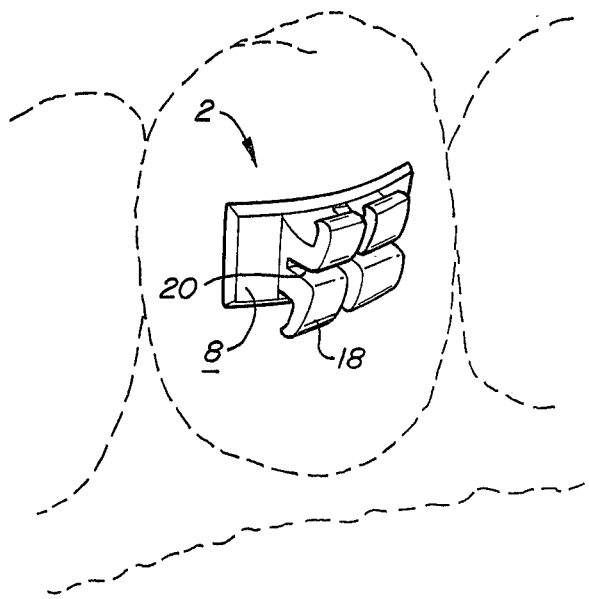
FIG._1.
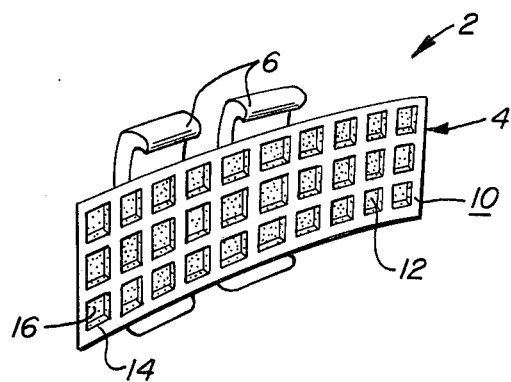
FIG._2.

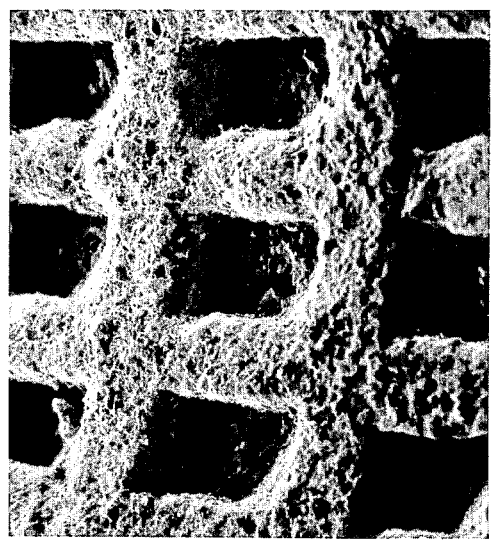
FIG._3.
FIG._4.

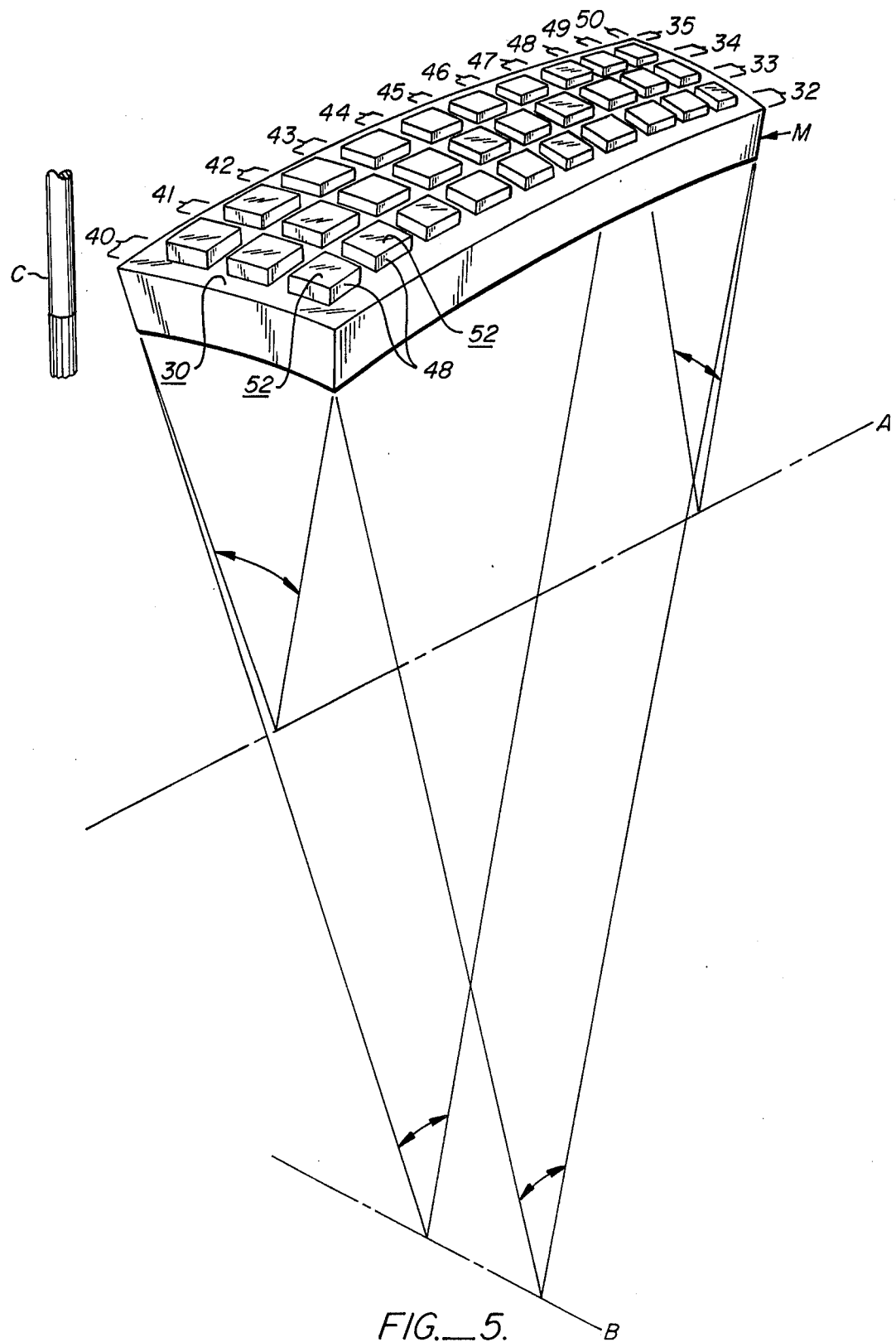
FIG._5.

ORTHODONTIC BRACKET ASSEMBLY

This is a continuation-in-part application of U.S. patent application Ser. No. 203,826, filed Nov. 3, 1980, now U.S. Pat. No. 4,369,033, issued Jan. 18, 1983.

BACKGROUND OF THE INVENTION

This invention relates to orthodontic appliances, particularly to orthodontic brackets of the type which are bonded to the external surface of the user's teeth.

Orthodontic brackets which are fastened to the surface of the wearer's teeth by being bonded directly thereto have become quite common. These brackets are typically attached to the outer surface of a pad having an opposite surface configured to generally conform to the shape of the wearer's tooth. This inner, or tooth abutting, surface of the bracket pad is adapted to be attached to the wearer's tooth, such as by adhesive.

One problem with using these bonded orthodontic brackets is a propensity of the pads to break away from the tooth. Among the ways to increase the bonding strength between the adhesive and the bracket is to form the pads with holes through their thickness. This allows adhesive to flow from the tooth abutting surface of the bracket pad, through the hole and on to the outer surface of the bracket pad. In this manner, the adhesive will form a strong mechanical bond between the bracket pad and tooth. However, it has been found that the adhesive on the outer surface of the pad can be worn away during brushing and thus lose much of its gripping power. Further, the desire for an intimate bond between the bracket pad and the adhesive is not addressed in this approach.

Another approach for increasing the bonding strength between the adhesive and the bracket is to sandblast the tooth abutting surface of the bracket pad and/or chemically etch the surface to produce bulbous pores on the tooth abutting pad surface. Either or both of these proceedures can be relatively expensive and also fail to significantly increase the total surface area of the pad to which the adhesive can be bonded.

A third manner of increasing the strength of the bond is to incorporate a wire mesh on the bracket pad and the tooth abutting surface. This again is relatively expensive and can result in a bracket which is thicker than desirable.

Examples of orthodontic brackets incorporating the features described above can be found in U.S. Pat. Nos. 3,765,091; 4,068,379; 4,100,678; and 4,165,561.

SUMMARY OF THE INVENTION

A cast orthodontic bracket assembly for bonding to the surface of a tooth and having a plurality of cavities within the tooth abutting surface of the bracket is disclosed. The walls of the cavities are provided with irregularities to enhance the bonding strength between the bracket and the tooth. It is preferred that the cavity walls be provided with surface irregularities from the process of casting the bracket. By the proper choice of cavity size and finishing techniques the cavity walls of a cast bracket can be retained in substantially the as-cast condition while the remaining surfaces of the bracket assembly are finished to the desired smoothness. As a result, the cavities provide surfaces to which conventional adhesives can be applied that produce heretofor unattainable bonding characteristics.

While prior art orthodontic brackets have been formed with cavities in the tooth abutting surface, such brackets have met with little commercial success because of the limited surface available for adhesive attachment. It has now been found that by casting the bracket with cavities in the tooth abutting surface, the natural casting irregularities imparted to the surface of the cavities produce substantially greater area for adhesive contact. Greater bonding strength results. The casting irregularities of the cavity walls also aid the mechanical bonding strength of the adhesive/bracket cavity wall bond.

As used in the application the terms cast and casting include various methods employing molds or dies. These methods include investment casting, die casting, powdered metallurgy and metal injection molding.

Metal injection molding is a commercially available process similar to both injection molding and powdered metallurgy. Powdered metal is combined with a plastic binding agent. The mixture is heated to a fluid state. The fluid mixture is injected into molds to form "green" molded parts. The green parts are then subjected to low temperatures sintering to drive off the binding agent. The parts are then subjected to high temperature sintering to allow intimate bonding between the metal particles. Metal injection molding has been found to be an effective method for casting the bracket. Metal injection molding equipment can be purchased from Witec California Incorporated of San Diego, California.

Also disclosed is a novel method of forming the cavities on the tooth-abutting surface of the bracket pad. In casting the brackets, molds are made which are the inverse of the finished bracket. The tooth abutting surface generally has a critical, compoundly curved surface shape for the best bonding to the tooth surface. According to the disclosed method for forming the mold, the cavities are formed by cutting two perpendicular series of parallel cuts in the mold. Since the base of these cuts form the tooth abutting surface, the depth of the cuts must be carefully controlled.

To form the cuts having the desired variable depths, the molds are mounted so that they can move along an arc corresponding to the desired shape of the tooth-abutting surface. After a cut is made, the mold is indexed about a first axis in space, the radius from the axis to the bracket corresponding to the instantaneous radius of curvature of the desired tooth-abutting surface. A new cut is made parallel to the previous cut and along the desired arc to achieve the desired depth of cut. Generally the arcs of the cuts are circular so that the cuts can be made by moving the bracket (or the cutting tool) along a circular arc; however, they need not be circular. After the entire series of parallel cuts is made, the mold is rotated 90° and a second series of parallel cuts is made about a second set of axes.

The resulting cavities in the bracket, formed when the discribed mold is used in a casting process to produce the bracket, are slightly larger at the bottom than at the top due to the rotation of the mold about the first axis to produce the parallel cuts. The bonding strength between the adhesive and the bracket pad is therefore increased.

The entire orthodontic bracket is preferably cast as a single element with a plurality of cavities preformed into the tooth abutting surface of the bracket pad. Provision of an orthodontic bracket cast as an integral unit provides a small, strong and accurately reproduced bracket at low cost.

The cast orthodontic bracket is placed in a tumbler having an abrasive material to remove sharp edges and flashing on the casting as well as to smooth the surface of the bracket. Smoothing the relatively rough cast surface is desirable for aesthetic reasons and for the comfort of the wearer. The particle size of the abrasive is chosen so that the surfaces of each cavity, i.e., the cavity walls, are not abraded smooth but are left in their roughened, as-cast state. After tumbling to smooth the exterior surface, the orthodontic bracket can be placed in a second abrasive medium for polishing. During polishing the interior surface of the cavities remains substantially unaffected by the polishing abrasive, while the external surface is further smoothed to the desired degree of luster.

The disclosed method for smoothing and polishing the exterior surface of the bracket is inexpensive and very effective. It has been found that no special precautions, other than judiciously choosing the tumbling abrasive, need be taken with regard to the cavities. The competing interests of a smooth exterior surface versus a roughened bonding surface are thus effectively balanced in a simple and inexpensive manner.

Other features and advantages of the present invention will appear from the following description in which the preferred embodiment has been set forth in detail in conjunction with the accompanying drawings.

BRIEF DESCRIPTION OF THE DRAWINGS

FIG. 1 is an enlarged perspective view of the orthodontic bracket shown bonded to the exterior surface of a tooth, the tooth shown in dotted lines.

FIG. 2 is an enlarged perspective view of the orthodontic bracket illustrating the plurality of cavities formed within the tooth abutting surface of the bracket pad.

FIG. 3 is a photograph taken through an electron microscope of the tooth abutting surface in its as-cast condition.

FIG. 4 is a photograph taken through an electron microscope of the tooth abutting surface after tumbling showing the cavity walls still in their as-cast condition.

FIG. 5 is a perspective view of a portion of the mold illustrating the manner of making the cuts in the mold to produce the cavities.

DETAILED DESCRIPTION OF THE PREFERRED EMBODIMENT

As shown in the figures, the orthodontic bracket 2 of the present invention includes generally a curved rectangular bracket pad 4 and a pair of archwire brackets 6 extending from the outer surface 8 of the bracket pad.

The bracket pad has an inner tooth abutting surface 10 opposite outer surface 8. The tooth abutting surface has a plurality of cavities 12 formed therein and extending into the interior of the bracket pad. The cavities, shown best in FIGS. 2 through 4, form a waffle-like pattern along surface 10. The cavities are defined by four cavity sides 14 and a cavity bottom 16. Collectively the cavity sides and cavity bottom are termed the cavity walls.

Archwire brackets 6 are of standard configuration and include a pair of L-shaped members 18 defining an archwire wire groove 20 therebetween. It is preferred to cast the orthodontic bracket as a single piece for both strength and economy.

The cavities are preferably formed by creating a mold wherein grooves are cut in the bracket pad portion of the mold. Since the mold is the inverse of the bracket, a cavity in the mold corresponds to a solid portion on the bracket and visa versa. Turning to FIG. 5, the method of producing the waffle-like tooth abutting surface 10 of bracket pad 4 will be described.

FIG. 5 schematically illustrates the formation of the proper surface shape of mold portion M. Surface 30, which corresponds to tooth abutting surface 10 of the bracket pad, is formed by first making four cuts 32-35. Cut 32 is made in the following manner. Mold portion M is indexed on an arc about axis A to positione a cutter C at one end of the proposed cut. Portion M is rotated about axis B to make cut 32 by the cutter. Mold portion M is indexed about axis A to align the cutter with proposed cut 33 and the procedure is repeated. After cuts 32-35 are made, mold portion M is rotated 90° so that transverse cuts 40-50 can be made in the manner indicated above. The transverse cuts are generally made about new axes A' and B', not shown, so that surface 30 will produce a tooth abutting surface 10 of the bracket having an appropriate compound contour for the best bonding to the tooth.

By making the cuts as described above, projections 48, which form the cavities in the molded bracket, are slightly smaller at their bases adjacent surface 30 than at their top surfaces 52. Therefore, the resulting cavities are slightly narrower at their bottoms than at their tops to enhance the strength of the bond.

The above described method of producing the mold produces cavity sides 14 which are generally perpendicular to tooth abutting surface 10 and further produces surface irregularities on sides 14 which are perpendicular to sides 14. These irregularities produced by the novel mold production technique therefore greatly enhance the bonding strength between the adhesive and cavity sides 14 compared with cavities having surface irregularities not so directed.

In lieu of moving the mold portion M, the cutter could be indexed and rotated about the axes. If desired the mold portion can be indexed about axis A and the cutter can be moved about axis B. Also, the movement of the cutter or mold portion while making the various cuts can be along paths which are not circular depending upon the shape of the tooth abutting surface desired. The mold may also be rotated an angle other than 90° so that the cavities produced will be diamond-shaped rather than rectangular.

The cavity walls are left in their roughened, as-cast state. This is accomplished by first tumbling the cast bracket in an abrasive medium, the particles of which are of sufficient size so that the cavity walls remain substantially unaffected. However, the remainder of the exterior surface of the bracket, that is the exterior surface other than the cavity walls, is smoothed by the tumbling in the abrasive medium. One particular tumbling method uses triangular shaped rocks in a water bath. The rocks are approximately ten times the size of the brackets. The brackets, rocks and water are placed in a vibrator to constantly agitate the contents to smooth the exterior surfaces.

Polishing the balance of the smoothed surface to produce the desired luster can be accomplished by tumbling in a polishing medium. This can be done by using stainless steel shot in a water bath. The shot is of different sizes, the smallest typically a number of times as large as a bracket. The shot, water and brackets are agitated in a vibrator until the exterior surfaces achieve the desired luster. Of course other appropriate tumbling methods, media and sizes of media can be used for the preliminary or finish tumbling steps.

FIGS. 3 and 4 show in a striking manner the effects of the above described structure and process. While the upper areas of the tooth abutting surface of FIG. 4 are relatively smooth, the cavity walls effectively retain their as-cast character.

Modification and variation may be made to the preferred embodiment without departing from what is regarded as the subject of the invention as defined in the following claims. For example, the cavities may be round and dispersed randomly over the tooth abutting surface of the bracket pad. Also, some or all of the cavities may extend entirely through the bracket pad.

What is claimed is:

1. An improved orthodontic bracket of the type including a pad having a surface adapted to be bonded to the exterior surface of a tooth, the pad having a tooth abutting surface with a plurality of cavities, said cavities defined by cavity walls, said bracket produced by a process comprising the following steps:
   casting said bracket as a unitary piece with the surface of said bracket having a cast irregular surface character, said casting step comprising the step of metal injection molding said bracket;
   providing an abrasive medium; and
   tumbling said cast bracket in the abrasive medium, the particles of the abrasive medium adapted so as not to smooth over the walls of said cavities but to smooth a substantial portion of the remainder of said tooth abutting surface and of said bracket surface.

2. The bracket produced by the process of claim 1 further comprising the step of polishing said smoothed bracket surface of said tumbled bracket.

3. The bracket produced by the process of claim 2 wherein the polishing step includes the step of polish tumbling said bracket.

4. A method for producing an orthodontic bracket of the type having a pad with cavities formed in a tooth abutting surface of the pad for bonding to a tooth, the cavities defined by cavity walls, the method comprising:
   forming a bracket mold with mold surfaces having a roughened surface character;
   casting the bracket in the bracket mold, the surfaces of the bracket having a roughened cast surface character, said casting step comprising the step of metal injection molding said bracket;
   providing an abrasive tumbling medium including abrasive particles;
   tumbling the bracket in the abrasive medium; and
   said providing step including the step of sizing the particles of the abrasive medium so the cavity walls are substantially unaffected by the abrasive medium and the remainder of the bracket surfaces are substantially smoothed over by the abrasive medium.

5. The bracket producing method of claim 4 further comprising the step of polish tumbling the bracket in a polish medium after the tumbling step.

6. The bracket producing method of claim 4 wherein said forming step includes the step of forming a bracket mold adapted to make a one-piece cast bracket.

* * * * *